United States Patent
Ligon, Jr.

[11] Patent Number: 5,328,663
[45] Date of Patent: Jul. 12, 1994

[54] APPARATUS FOR THE TRAPPING OF REACTION PRODUCTS

[75] Inventor: Woodfin V. Ligon, Jr., Schenectady, N.Y.

[73] Assignee: General Electric Company, Schenectady, N.Y.

[21] Appl. No.: 57,907

[22] Filed: May 7, 1993

[51] Int. Cl.⁵ ........................................... G01N 31/12
[52] U.S. Cl. ...................................... 422/78; 422/307; 432/210; 432/225; 436/160; 436/155
[58] Field of Search ............... 422/232, 233, 198, 307, 422/261, 202, 312, 197, 78; 432/225, 210; 203/4; 55/220, 235–236, 239; 96/193–194, 202; 436/155, 160

[56] References Cited

U.S. PATENT DOCUMENTS

| | | | |
|---|---|---|---|
| 3,905,770 | 9/1975 | Mossberg | 422/78 |
| 4,352,659 | 10/1982 | Salmela et al. | 432/225 |
| 4,401,763 | 8/1983 | Itoh | 422/78 |
| 4,914,037 | 4/1990 | Forster et al. | 422/78 |
| 5,087,422 | 2/1992 | Friese et al. | 422/78 |
| 5,174,746 | 12/1992 | Kemori | 432/210 |

OTHER PUBLICATIONS

DIN 53436, Teil, 1981.

Primary Examiner—Robert J. Warden
Assistant Examiner—Hien Tran
Attorney, Agent, or Firm—William H. Pittman

[57] ABSTRACT

A device for trapping reaction products and especially for generating and trapping decomposition products from thermal decomposition processes, including combustion, is described. Decomposition products of a solid sample are formed at the top end of an externally heated vertical decomposition tube and are channeled downward through a region of decreased diameter in which a trapping device is positioned. The trapping device consists of two vertical concentric tubes of which the top end of the inner tube is slightly lower than that of the outer tube. Water flows upward between the two concentric tubes, traps the decomposition products at the top, and drops down through the inner concentric tube. Products contained in the water are collected externally from the lower end of the trapping device for analysis. The insoluble gaseous products are collected by an external vacuum system after passing through the stream of water.

16 Claims, 2 Drawing Sheets

APPARATUS FOR THE TRAPPING OF REACTION PRODUCTS

The present invention generally relates to an apparatus for the trapping of reaction products, and more particularly to an apparatus for thermal decomposition of solid samples and the trapping of resulting products for analysis.

BACKGROUND OF THE INVENTION

A common analytical procedure is the trapping and analysis of reaction products. Testing and evaluating the toxicity of combustion products emitted by fires, for example, has led to the development of various devices for simulating combustion conditions and collecting the products. The accuracy of subsequent qualitative and quantitative analyses of the combustion products depends on whether the products have been modified before collection and on whether substantially all the products have been trapped and collected.

Combustion product analysis is not limited to determining the amount of carbon dioxide, carbon monoxide, oxygen and water generated, but includes the identification and quantification of biologically hazardous materials contained in the products for toxicity studies. For example, the characterization of the products emitted from burning polymers is necessary for limiting the use of polymers in certain applications.

In addition to combustion product analysis a need exists for the testing of products generated by other chemical reactions, especially high temperature decomposition processes. For example, pyrolysis and certain metallurgical processes such as sintering may emit toxic products requiring identification.

Thus, a device for the efficient and accurate collection of various chemical reaction products and especially for the creation and trapping of products formed by combustion and high temperature decomposition processes is necessary for meaningful subsequent analysis.

The generation and collection of thermal combustion products for analysis has commonly been accomplished using devices which incorporate the method described in DIN 53436. Such devices consist of a long, horizontal quartz combustion tube in which a sample placed in an airstream is continuously decomposed by means of an external moving furnace. The effluents are carried by the airstream from the tube to an external analytical measuring system or, alternatively, are measured by on-line monitors such as infrared detectors.

Problems associated with using the DIN 53436 apparatus include inaccurate qualitative and quantitative analyses of the decomposition products due to the great amount of soot and smoke emitted during combustion of the sample. Such materials strongly adhere to surfaces even slightly cooler than the region in which they were generated. Thus, not all the decomposition products will exit the tube for analysis, and results will be inaccurate. Conventional solvent washing of the combustion tube to collect the adhered material will not increase accuracy because much of the product may polymerize upon contact with the cooler walls of the decomposition tube and remain adhered to the surface.

Another source of error in the analysis of the decomposition products comes from the long transportation time (typically between 25 and 35 minutes) between sample decomposition and product collection. Since the products remain heated at high temperatures while they are slowly carried along the length of the tube, the initial products may polymerize or otherwise be altered before analysis. Thus, the results obtained may include identification of species not actually produced during sample decomposition.

Finally, cleaning the apparatus following the decomposition process is both time-consuming and cumbersome. Since solvent washing will not remove the surface contamination, the components of the device must be reheated in oxygen to temperatures approximating 500° C. to burn off the polymer. Thus, evaluation of multiple samples on the same apparatus in a short amount of time is impossible.

The present invention is a device designed in part to overcome the problems encountered when using conventional apparatus, such as that employed according to DIN 53436 for trapping thermal decomposition products. Sampling of both the organic and inorganic components is more accurate because all the product is collected without modification. The total time from decomposition of the sample to collection is typically less than 10 min; therefore, the products are not likely to polymerize before collection. Also, the apparatus maintenance and cleaning time is greatly reduced.

Reaction gases are channeled from top to bottom of an externally heated vertical external tube by slightly pressurizing the products. Thus, the products do not adhere to the inner walls of the external tube but are forced into a region of decreased diameter at the lower end of the tube. Two concentric tubes reside within the narrow portion of the external tube to trap the products. Introduction of a shield gas at the lower end of the external tube prevents product adherence to both the decreased diameter portion of the external tube and the concentric tubes. The concentric tubes are flushed with water and cooled such that soluble decomposition products are trapped in the water and collected for analysis. Insoluble products remain suspended in the water and may be separated externally. The gaseous products are collected by vacuum after passing through the stream of water.

The use of water in the present invention to trap the reaction products is advantageous in that system temperatures much greater than 1000° C. may be reached in heating the sample. By using an external tube and a sample introduction apparatus consisting of a ceramic material which is heat resistant at high temperatures, the system is made adaptable to such decomposition processes as combustion, sintering or pyrolysis. Because the water cools the concentric tubes through which the products pass before leaving the system, the concentric tubes and the collection vessel may consist of a material such as quartz or glass that is not physically resistant to very high temperatures.

Trapping the reaction products with water is also advantageous because, for example, the actual physiological situation where combustion products are breathed into the lungs is more accurately simulated in the present invention that in the DIN 53436 device. Finally, in the case of combustion where water is a major product of the process, its introduction to trap the sample product adds no new components to the product composition.

SUMMARY OF THE INVENTION

Therefore, the invention is an apparatus for trapping reaction products, said apparatus comprising:

(I) a vertical external tube adapted to contain or receive reaction products, said external tube having a region of decreased diameter near the lower end thereof;
(II) first gas inlet means for supplying a first gas near the upper end of said external tube;
(III) second gas inlet means for supplying an inert shield gas near the lower end of said external tube and below said region of decreased diameter; and
(IV) trapping means for reaction products, comprising:
(A) an outer tube adapted for sealable connection to the lower end of said external tube with the upper end of said outer tube being located in said region of decreased diameter;
(B) an inner concentric tube in said outer tube, the upper end of said inner tube being at a lower level than that of said outer tube;
(C) water supply means adapted to provide an upward-moving stream of flush water in said outer tube at a flow rate sufficient to maintain contact with substantially the entire inner surface of said outer tube and then to flow into said inner tube;
(D) a collection vessel adapted to receive all of said flush water and reaction products, said collection vessel communicating with the lower end of said inner tube; and
(E) vacuum means attached to said collection vessel to receive said first and shield gases.

The invention is of particular utility for the generation and trapping of decomposition (e.g., combustion) products. Therefore, in a preferred embodiment said external tube is heat-resistant and said apparatus also comprises:

heat-resistant sample-containing means for holding a decomposition sample, said sample-containing means being sealably connected to the upper end of said external tube;

sample displacement means for moving said sample vertically in said external tube in locations above said region of decreased diameter; and heating means for heating said external tube, sample and region of decreased diameter to a sample decomposition temperature.

DETAILED DESCRIPTION

Figure 1:
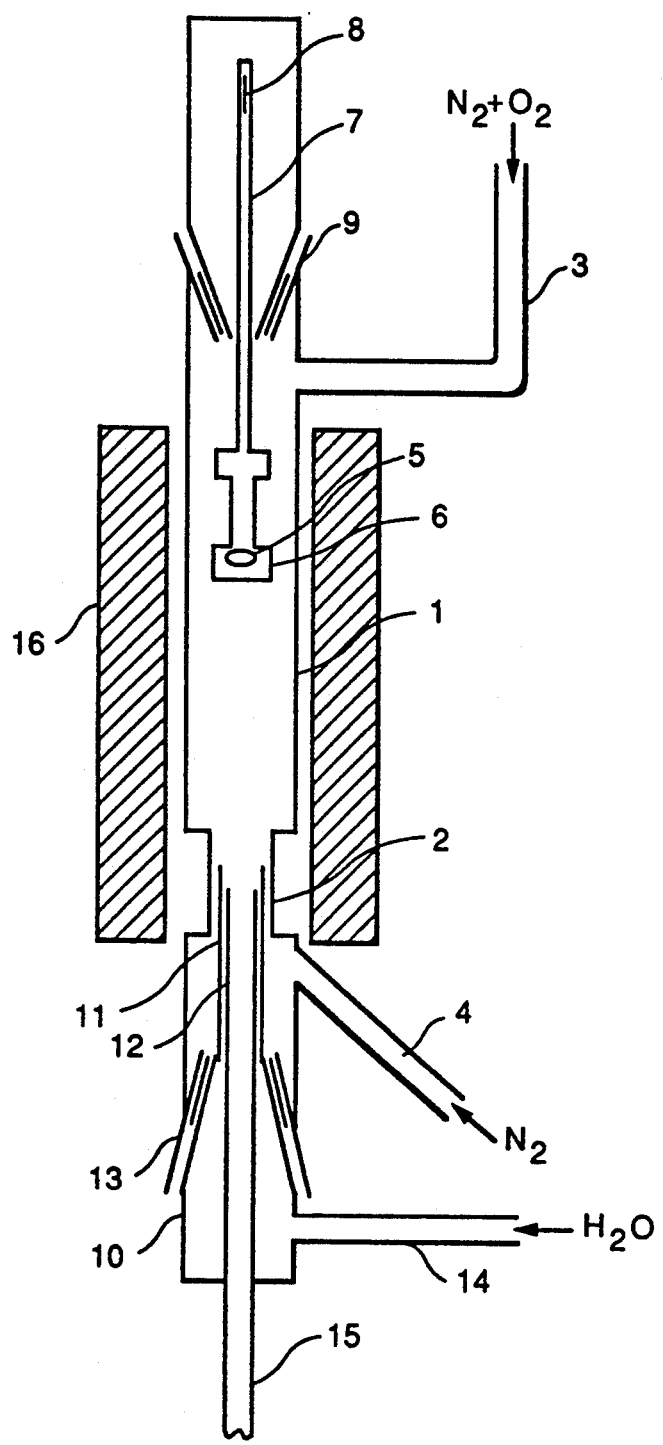
FIG. 1 is a partial view of an apparatus of the preferred embodiment.

Referring to the drawings, FIG. 1 shows an apparatus of the preferred embodiment of the invention; however the collection vessel is omitted. A vertical external tube, indicated generally by numeral 1, is adapted to contain or receive reaction products. It is typically employed in many situations as a decomposition or combustion tube, and will frequently be designated "decomposition tube" hereinafter.

In said preferred embodiment, decomposition tube 1 is situated vertically within a means for heating the sample such as furnace 16. For a solid sample of approximately 220 mg a suitable decomposition tube would typically have a length of 45 cm and an inner diameter of 30 mm. Corresponding dimensions for samples of other sizes will be apparent to those skilled in the art, or may be determined by simple experimentation.

The lower end of the decomposition tube contains a region 2 of decreased inner diameter; for example, 19 mm. Further, decomposition tube 1 is generally made of a heat resistant material such as quartz for combustion processes occurring at temperatures between 400° and 1000° C. or a ceramic material which can withstand temperatures greater than 1000° C. for high temperature decomposition processes such as sintering or pyrolysis.

Gas inlet port 3 is at the upper end of the decomposition tube 1. Below decreased diameter portion 2 is a second gas inlet 4.

Heat resistant sample boat 6, shown as containing sample 5, in the top end of decomposition tube 1 is attached to the lower end of heat resistant rod 7. The top end of rod 7 is equipped with bar 8 of ferromagnetic material such as iron or steel. Boat 6 and rod 7 may be made of quartz of ceramics depending on the temperature to which it will be exposed. This assembly is attached to the top end of decomposition tube 1 by a sealable connecting device 9 such as a ground glass joint.

Trapping device 10 consists of two concentric tubes 11, 12 of which the outer tube 11 sealably connects with the bottom end of the decomposition tube 1 using, for example, a standard ground glass joint 13. The top end of outer tube 11 is positioned within region 2 of decreased diameter. The upper end of inner concentric tube 12 is lower than the top end of outer concentric tube 11. Water inlet 14 is at the lower end of trapping device 10.

Because trapping device 10 is cooled by water, it is not necessary that its components be made of a material that is heat resistant at temperatures above 1000° C. Instead, a material such as glass which softens a lower temperatures may be used for the trapping device. However, the composition of the reaction products being trapped must be considered when choosing a material for inner concentric tube 12. Because said products come directly in contact with inner concentric tube 12, it is important that it not react with said products. For example, if it is known that the reaction products contain materials such as HF that erode the surface of glass, inner concentric tube 12 may be made of a material such as polytetrafluoroethylene.

Outlet end 15 of inner concentric tube 12 extends into a collection vessel, shown in FIGS. 2 and 3 and described hereinafter. The collection vessel can be made of any material that is unreactive with the products, such as glass or tetrafluoroethylene.

Sample 5 and decomposition tube 1, including region 2 of decreased diameter, are heated by furnace 16 or other appropriate heating means.

Figure 2:
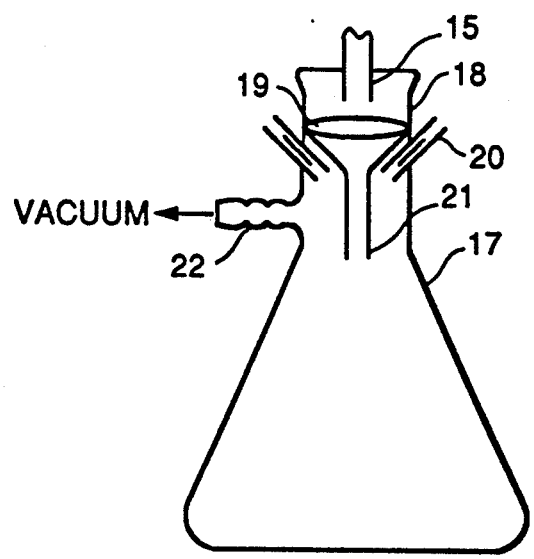
FIGS. 2 and 3 are views of two illustrative collection vessels.

FIG. 2 shows, as a collection vessel in the preferred embodiment of the invention, a filter flask 17. Outlet end 15 of inner concentric tube 12 extends into the top end of Buchner funnel 18 containing glass fiber filter 19. Buchner funnel 18 rests on the top end of filter flask 17 using a sealably connecting device 20 such as a ground glass joint or rubber stopper. Outlet 21 of Buchner funnel 18 is directed into the body of filter flask 17. Vacuum is applied at outlet 22 of filter flask 17.

Figure 3:
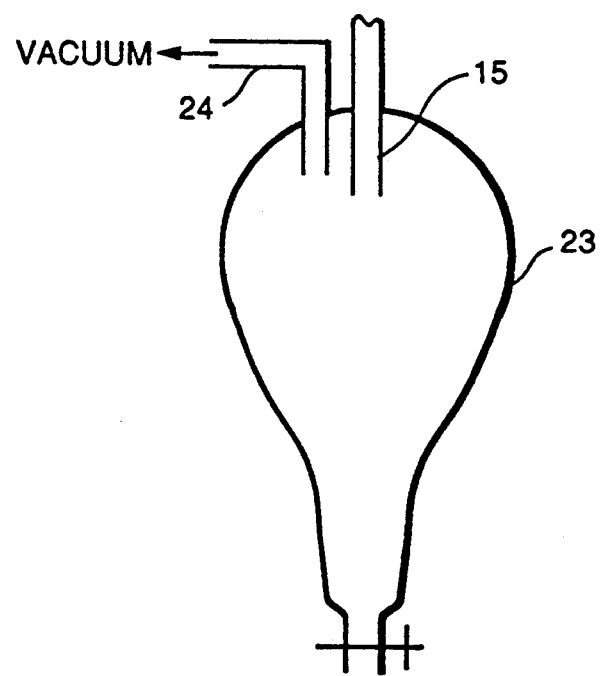

FIG. 3 shows, as an alternative collection vessel, separatory funnel 23. Outlet end 15 of inner concentric tube 12 extends into the top end of said separatory funnel. Vacuum is applied at outlet 24. To those skilled in the art it will be obvious that other collection vessels may be used.

Operation of the present invention begins by heating decomposition tube 1 to the desired decomposition temperature by means of furnace 16. Deionized water is pumped into trapping device 10 via inlet 14, typically at a rate of about 150 ml/min, passes upward between concentric tubes 11, 12 and finally drops down through inner concentric tube 12. Although the water employed is typically deionized water, it will be designated "water" hereinafter. Shield and decomposition gases are introduced through corresponding inlets 3 and 4, respectively. Vacuum is applied at outlet 22 where the collection vessel is filter flask 17 or at outlet 24 where the collection vessel is separatory funnel 23.

Sample boat 6 containing sample 5 for decomposition is lowered into heated decomposition tube 1 externally using magnetic bar 8. Sample 5 thermally decomposes, and the products are forced downward through decomposition tube 1 by the positive pressure exerted by the gas entering through inlet 3. For combustion processes the decomposition gas could be $O_2$ or a mixture of $N_2$ and $O_2$, such as air, but in other decomposition processes an inert gas such as $N_2$ could be substituted. The decomposition products are channeled through region 2 of decreased diameter where they are trapped by the water flowing through trapping device 10.

The upper end of inner concentric tube 12, being lower than the top end of outer concentric tube 11, directs the water that is pumped upward between concentric tubes 11, 12 downward through inner concentric tube 12. The required relative positions of the tops of the two tubes are determined by the natural meniscus formed by the water as it flows into inner concentric tube 12. Outer concentric tube 11 is cut to a suitable height, typically within 1 mm above the meniscus. As apparent to those skilled in the art, the rate of water pumped into the system as well as the aforementioned relative tube positions may be altered to provide sufficient water flow.

An inert shield gas such as $N_2$ is introduced through inlet port 4 to prevent adherence of the decomposition products to both the inner surface of decomposition tube 1 in region 2 of decreased diameter and the exterior surface of outer concentric tube 11. Thus, the decomposition products are constrained by pressures exerted by the gas introduced through inlet 3 and by the shield gas introduced at inlet 4 to converge on the top end of trapping device 10 where they are trapped by the flowing water.

Decomposition products contained in the water, both soluble and insoluble, pass through inner concentric tube 12 and from outlet end 15 into collection vessel 17 or 23 for subsequent analysis. Where the collection vessel used is filter flask 17, the water is first directed through glass fiber filter 19, typically contained in Buchner funnel 18. Water soluble inorganic materials such as HBr, HCl, HCN, etc. are pulled with the water through glass fiber filter 19 by means of a vacuum at outlet 22 and are thus contained in the filter flask solution. The vacuum at outlet 22 also pulls the insoluble decomposition product gases and shield gas from the system into an evacuated external tank (not shown) for analysis. The insoluble particulate decomposition products that were suspended in the water remain on the filter. Organic decomposition products adhering to the filter can typically be recovered by washing the filter with organic solvent.

In an alternative embodiment the water can be collected directly in a vessel such as separatory funnel 23.

Organic solvent may be added and mixed with the collected water to separate the organic products from the water soluble inorganic products. The organic layer may then removed for analysis. The particulate material can be recovered by subsequent filtering of the water layer. Vacuum is applied at outlet 24 attached to separatory funnel 23 to collect the insoluble gases.

What is claimed is:

1. Apparatus for trapping reaction products, said apparatus comprising:
   (I) a vertical external tube having an upper and lower end and having a region of decreased diameter;
   (II) heat-resistant sample-containing means for holding a decomposition sample above said region of decreased diameter, said sample-containing means being sealably connected to the upper end of said external tube;
   (III) sample displacement means for moving said sample vertically in said external tube in locations above said region of decreased diameter;
   (IV) heating means for heating said external tube including said region of decreased diameter, and said sample-containing means to a sample decomposition temperature;
   (V) first gas inlet means for supplying a first gas to the upper end of said external tube;
   (VI) second gas inlet means for supplying an inert shield gas to the lower end of said external tube below said region of decreased diameter; and
   (VII) trapping means for trapping reaction products, comprising:
      (A) an outer tube having an inner surface and sealably connected to the lower end of said external tube, and an upper end of said outer tube being located in said region of decreased diameter;
      (B) an inner concentric tube in said outer tube, an upper end of said inner tube being at a lower level than that of said outer tube;
      (C) water supply means providing an upward-moving stream of flush water in said outer tube at a flow rate sufficient to maintain contact with substantially the entire inner surface of said outer tube and then to flow into said inner tube;
      (D) a collection vessel communicating with the lower end of said inner tube; and
      (E) vacuum means attached to said collection vessel to receive said first and shield gases.

2. Apparatus according to claim 1 wherein said external tube is of a heat-resistant material.

3. Apparatus according to claim 1 wherein said external tube, said first gas inlet means, and said second gas inlet means are of quartz.

4. Apparatus according to claim 1 wherein said external tube, said first gas inlet means, and said second gas inlet means are of a ceramic material.

5. Apparatus according to claim 1 wherein said sample-containing means is of quartz.

6. Apparatus according to claim 1 wherein said sample-containing means is of a ceramic material.

7. Apparatus according to claim 1 wherein the seals connecting said sample-containing means with said external tube are ground glass joints.

8. Apparatus according to claim 1 wherein said sample displacement means is of quartz.

9. Apparatus according to claim 1 wherein said sample displacement means is of a ceramic material.

10. Apparatus according to claim 1 wherein said sample displacement means attaches to and contains a ferromagnetic rod distal to said sample-containing means allowing said sample-containing means to be moved magnetically.

11. Apparatus according to claim 1 wherein said trapping means is of quartz.

12. Apparatus according to claim 1 wherein said trapping means is of glass.

13. Apparatus according to claim 1 wherein said inner concentric tube is of polytetrafluoroethylene.

14. Apparatus according to claim 1 wherein said collection vessel is a combination of filter and filter flask.

15. Apparatus according to claim 1 wherein said collection vessel is a separatory funnel.

16. Apparatus according to claim 1 wherein said heating means is a tubular furnace.

* * * * *